(12) United States Patent
Sekiya et al.

(10) Patent No.: US 6,919,455 B2
(45) Date of Patent: Jul. 19, 2005

(54) PURINE DERIVATIVE DIHYDRATE, DRUGS CONTAINING THE SAME AS THE ACTIVE INGREDIENT AND INTERMEDIATE IN THE PRODUCTION THEREOF

(75) Inventors: Kouichi Sekiya, Kisarazu (JP); Akihiro Takemiya, Yokohama (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 10/631,795

(22) Filed: Aug. 1, 2003

(65) Prior Publication Data

US 2004/0077665 A1 Apr. 22, 2004

Related U.S. Application Data

(62) Division of application No. 09/926,477, filed as application No. PCT/JP00/02952 on May 9, 2000, now Pat. No. 6,660,745.

(30) Foreign Application Priority Data

May 11, 1999 (JP) ............................................. 11-129499

(51) Int. Cl.[7] .................... C07D 473/40; C07D 473/36; C07D 473/28; C07F 9/6561
(52) U.S. Cl. .......................... 544/265; 544/244; 544/264
(58) Field of Search ............................... 544/244, 264, 544/265

(56) References Cited

U.S. PATENT DOCUMENTS

| | | | |
|---|---|---|---|
| 3,862,189 A | 1/1975 | Schwender | |
| 3,936,454 A | 2/1976 | Schwender | |
| 4,012,495 A | 3/1977 | Schmiechen et al. | |
| 4,193,926 A | 3/1980 | Schmiechen et al. | |
| 5,124,455 A | 6/1992 | Lombardo | |
| 5,770,611 A | 6/1998 | Brown | |
| 5,861,404 A | 1/1999 | Niewöhner et al. | |
| 5,948,913 A | 9/1999 | Yamamoto et al. | |
| 6,734,187 B1 * | 5/2004 | Tanaka et al. | 514/263.22 |

FOREIGN PATENT DOCUMENTS

| | | |
|---|---|---|
| CA | 2167353 | 7/1996 |
| EP | 1043324 | 10/2000 |
| JP | 8-231545 | 9/1996 |
| WO | 92/12961 | 8/1992 |
| WO | 93/23401 | 11/1993 |
| WO | 94/11004 | 5/1994 |
| WO | 94/12461 | 6/1994 |
| WO | 94/14742 | 7/1994 |
| WO | 95/00516 | 1/1995 |
| WO | 95/10525 | 4/1995 |
| WO | 95/18815 | 7/1995 |
| WO | 96/26209 | 8/1996 |
| WO | 96/26942 | 9/1996 |
| WO | 96/36606 | 11/1996 |
| WO | 99/24432 | 5/1999 |
| WO | 00/68231 | 11/2000 |

OTHER PUBLICATIONS

First Page of JP 4–253945.
First Page of JP50–157360.
First Page of JP 6–504782.
First Page of JP 9–500376.
First Page of JP 7–504442.
Angyal, A.M. et al., "Purines as Amplifiers of the Antibiotic Activity of Phleomycin Against *Escherichia coli* B," J. Gen. Microbiology, (1974), 85, 163–68.
Beavo, J.A., Multiple Isozymes of Cyclic Nucleotide Phosphodiesterase, Adv. Second Messenger Phosphoprotein Res., 22, 1–38 (1988).
Beavo, J.A. and Reifsnyder, D.H., Primary Sequence of Cyclic Nucleotide Phosphodiesterase Isozymes and the design of Selective Inhibitors, Trends Pharm. Sci., 11, 150–155 (1990).
Hidaka, H. and Shibuya, M., A New Assay of Cyclic Nucleotide Phosphodiesterase; its Application to Human Serum, Biochem. Med. 10, 301–311 (1974).
C.D. Nicholson, S.A. Jackman & R. Wilke, The ability of denbufylline cyclic nucleotide phosphodiesterase and its affinity for adenosine receptors and the adenosine re–uptake site, Br. J. Pharmacol, (1989), 97, 889–897.

(Continued)

Primary Examiner—Mark L. Berch
(74) Attorney, Agent, or Firm—Greenblum & Bernstein, P.L.C.

(57) ABSTRACT

A compound represented by the following formula (I), or a salt thereof:

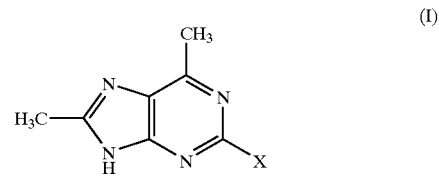

(I)

where X is a halogen atom or a group represented by —S—$(CH_2)_n$—A, —SO—$(CH_2)_m$—B, —$SO_2$—$(CH_2)_m$—B, —$OSO_2$—$(CH_2)_m$—B, —OCO—$(CH_2)_m$—B or —OPO(OR)—$(CH_2)_m$—B, wherein n represents an integer of 0–4, A represents an optionally substituted aromatic hydrocarbon group or an optionally substituted heterocyclic residue having 1 to 4 hetero atoms selected from an oxygen atom, sulfur atom and nitrogen atom and having 5 to 10 ring-constituent atoms, m represents an integer of 0–4, B represents an optionally substituted alkyl group, an optionally substituted aromatic hydrocarbon group or an optionally substituted heterocyclic residue having 1 to 4 hetero atoms selected from an oxygen atom, sulfur atom and nitrogen atom and having 5 to 10 ring-constituent atoms, and R represents an optionally substituted alkyl group.

5 Claims, No Drawings

OTHER PUBLICATIONS

Torphy, T.J. and Undem, B.J., Phosphodiesterase Inhibitors: New Opportunities for the Treatment of Asthma, Thorax, 46, 512–523 (1991).

Global Initiative for Chronic Obtructive Lung Disease (NIH, National Heart, Lung and Blood Institute) p. 6.

Makino et al., International Archives of Allergy and Immunology, 121(Suppliment 1) pp. 4, 5, 54, 33, 36–39(2000).

Benjamin K. Gill, "Diagram Representing the Roles of Cytokines in Inflammatory Responses" http://attila.stevens-tech.edu/chembio/bgill/IL 10K.html.

* cited by examiner

PURINE DERIVATIVE DIHYDRATE, DRUGS CONTAINING THE SAME AS THE ACTIVE INGREDIENT AND INTERMEDIATE IN THE PRODUCTION THEREOF

CROSS-REFERENCE TO RELATED APPLICATIONS

This application is a divisional of application Ser. No. 09/926,477, which has a 371 date of Jan. 9, 2002 now U.S. Pat. No. 6,660,745, which is a National Stage Application of International Application No. PCT/JP00/02952, filed May 9, 2000, which was not published in English under PCT Article 21(2), entering the National Stage on Nov. 9, 2001, and which claims priority of Japanese Application No. 11-129499, filed May 11, 1999. The entire disclosure of application Ser. No. 09/926,477 is considered as being part of this application, and the entire disclosure of application Ser. No. 09/926,477 is expressly incorporated by reference herein in its entirety.

TECHNICAL FIELD

The present invention relates to a novel purine derivative dihydrate with a phosphodiesterase IV inhibitory effect, to drugs containing the dihydrate as an active ingredient and to a method of using the drugs. The invention further relates to a compound useful as an intermediate in the production of the purine derivative dihydrate.

BACKGROUND ART

Cyclic AMP (cAMP) is an important second messenger which is involved in relaxation of respiratory tract smooth muscles and control of inflammatory cells, and the messenger is decomposed by phosphodiesterase (hereinafter abbreviated as "PDE" in the specification) to be converted into inactive 5'-AMP. Therefore, it is believed that suppression of the decomposition of cAMP by PDE may increase the concentration of cAMP, thereby bronchodilatation and anti-inflammatory action can be achieved. For this reason, PDE inhibitors having inhibitory action against the decomposition of cAMP have been focused as medicaments for the treatment of asthma, chronic obstructive pulmonary disease (hereinafter abbreviated as "COPD" in the specification) and/or other inflammatory diseases. In addition, five PDE isozymes (PDE I, II, III, IV and V) have recently been isolated, and their specific tissue distributions have been revealed (Adv. Second Messenger Phosphoprotein Res., 22, 1 (1988): Trends Pharm., Sci., 11, 150 (1990)).

Among inhibitors for these isozymes, in particular, inhibitors specific for PDE IV have been suggested to be possibly useful for the treatment of asthma, COPD and/or other inflammatory diseases (Thorax 46, 512 (1991) etc.). Herein, chronic articular rheumatism, atopic dermatitis, psoriasis, etc., are listed as concrete examples of the inflammatory disease. As a compound having specific inhibitory activity against PDE IV, for example, the compound disclosed in Japanese Patent Unexamined Publication (Kokai) No. 50-157360/1975 (Rolipram) has been known.

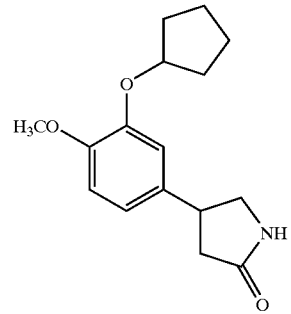

Although various compounds have been known as PDE IV inhibitors (for example, compounds disclosed in Japanese Patent Unexamined Publication (Kokai) No. 4-253945/1992, International Patent Publication in Japanese (Kohyo) Nos. 6-504782/1994, 7-504442/1995, 8-501318/1996 and 9-500376/1997 and so forth), they have not been used clinically so far, and development of novel compounds having PDE IV inhibitory activity has been desired.

DISCLOSURE OF THE INVENTION

As a result of diligent research directed toward providing a novel compound which has a specific inhibitory effect against PDE IV and is useful for asthma, COPD and/or other inflammatory diseases, the present inventors have found that specific purine derivatives have an excellent inhibitory effect against PDE IV (WO99/24432). Upon continued investigation, the present inventors discovered a specific purine derivative dihydrate with excellent stability as well as an intermediate useful for its production, and the present invention has thus been completed.

In other words, the present invention provides a dihydrate of 4-[[9-[(3-cyclopentyloxy-4-methoxy)benzyl]-6,8-dimethylpurin]-2-yl-3-oxypropyl]pyridine N-oxide and a process for its production.

According to another aspect, the invention provides drugs containing the dihydrate as an active ingredient thereof. Such drugs are preferably provided as pharmaceutical compositions containing the dihydrate and formulating additives, and may be used, for example, as preventives and/or remedies for asthma, COPD and/or other inflammatory diseases. According to yet another aspect, the invention provides the use of the aforementioned dihydrate for production of the aforementioned drugs; a remedy and/or preventive method for asthma, COPD and/or other inflammatory diseases which comprises a step of administering an effective dose of the dihydrate to a mamma ian animal including human; a PDE IV inhibitor containing the dihydrate; and a process for producing the dihydrate by treating anhydride crystals of 4-[[9-[(3-cyclopentyloxy-4-methoxy)benzyl]-6,8-dimethylpurin]-2-yl-3-oxypropyl]pyridine N-oxide under hydrous conditions.

According to still another aspect, the invention provides a compound represented by the following general formula (I):

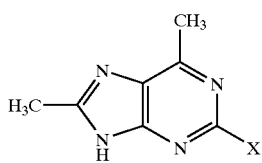

(I)

where X is a halogen atom or a group represented by —S—(CH$_2$)$_n$—A, —SO—(CH$_2$)$_m$—B, —SO$_2$—(CH$_2$)$_m$—B, —OCO—(CH$_2$)$_m$—B, —OCO—(CH$_2$)$_m$—B or —OPO(OR)—(CH$_2$)$_m$—B (wherein n represents an integer of 0–4, A represents an optionally substituted aromatic hydrocarbon group or an optionally substituted heterocyclic residue, m represents an integer of 0–4, B represents an optionally substituted alkyl group, an optionally substituted aromatic hydrocarbon group or an optionally substituted heterocyclic residue, and R represents an optionally substituted alkyl group), which is useful as an intermediate in the production of 4-[[9-[(3-cyclopentyloxy-4-methoxy)benzyl]-6,8-dimethylpurin]-2-yl-3-oxypropyl]pyridine N-oxide.

The invention further provides a compound represented by the following general formula (II):

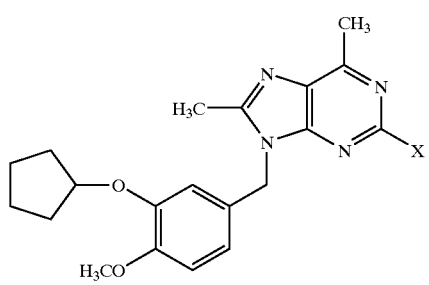

(II)

where X is as defined above. This compound is also useful as an intermediate in the production of 4-[[9-[(3-cyclopentyloxy-4-methoxy)benzyl]-6,8-dimethylpurin]-2-yl-3-oxypropyl]pyridine N-oxide.

BEST MODE FOR CARRYING OUT THE INVENTION

The dihydrate of the invention can be produced by treatment under hydrous conditions of anhydride crystals obtained by the process described in Example 5 of WO99/24432, for example. The hydrous conditions are not particularly restricted, and as an example, the production may be carried out by a process of dissolving the anhydride crystals in a hydrous organic solvent (such as hydrous isopropyl alcohol, for example) with warming and then cooling to room temperature for crystallization; a process of allowing the anhydride to stand for several weeks at room temperature under conditions with a relative humidity of 75% or greater; or a process of adding water to the anhydride heating with warming (for example, about 12 hours at 70° C.) and then cooling to room temperature. The dihydrate production process of the invention is of course not limited to treatment under these hydrous conditions.

The dihydrate of the invention has a specific inhibitory effect against PDE IV, and is useful as an active ingredient in drugs for asthma, COPD and/or other inflammatory diseases. In particular, the dihydrate of the invention is stable and has excellent physicochemical properties as an active ingredient for drugs. When the dihydrate of the invention is used as an active ingredient in a drug, the dihydrate itself may be administered directly or as a pharmaceutical composition prepared using pharmacologically acceptable formulating additives. The composition and form of the pharmaceutical composition is determined based on the route of administration, the administration plan, etc. For example, it may be prepared in the form of granules, powders, tablets, hard capsules, soft capsules, syrups, emulsions, suspensions, solutions or the like for oral administration or in the form of an injection for intravenous administration, intramuscular administration or subcutaneous administration. It may also be in the form of powders for injection and prepared at the time of use. Alternatively, it may be a composition for parenteral administration, such as a transdermal agent or transmucosal agent.

For the manufacturer of pharmaceutical compositions suitable for oral, enteral, parenteral, or topical administration, organic or in organic pharmaceutical additives can be used. These additives may be a solid or liquid, and examples include carriers end diluents for pharmaceutical formulations and the like. As excipients used for the manufacture of solid pharmaceutical compositions, for example, lactose, sucrose, starch, talc, cellulose, dextrin and the like can be used. For the manufacturer of liquid pharmaceutical compositions for oral administration such as emulsions, syrups, suspensions and solutions, commonly used inactive diluents, for example, water, vegetable oils and the like can be used. The pharmaceutical compositions may contain, for example, wetting agents, suspension aids, sweeteners, aromatics, colorants, preservatives and the like as auxiliaries, as well as inactive diluents. A liquid preparation may be prepared and filled in capsules made of a material that can be disintegrated in body such as gelatin. As solvents or suspending agents used for the manufacture pharmaceutical compositions for parenteral administration such as injections, examples include water, propylene glycol, polyethylene glycol, benzyl alcohol, ethyl oleate, lecitin and the like. Method for preparing the pharmaceutical compositions are not particularly limited, and any methods for preparing formulations available in the art can be utilized.

The drugs of the present invention may be used as remedies and/or preventives for asthma, COPD and/or other inflammatory diseases. The dose of the drugs according to the present invention will generally be 0.01–1000 mg and preferably 0.01–100 mg (weight of active ingredient) per day for adults when used for oral administration. The dose is, of course, more preferably adjusted depending on the conditions such as the age, condition and symptoms of the patient or the presence of any simultaneously administered drugs. The above-mentioned daily dose may be administered once a day, spread over two or three administrations per day at appropriate intervals, or intermittently over a period of several days. For use as an injection of drip infusion, a continuous or intermittent dose of 0.001–100 mg (weight of active ingredient) per day for adults is preferred.

The compounds represented by formulas (I) and (II) of the present invention are useful as intermediates in the production of 4-[[9-[(3-cyclopentyloxy-4-methoxy)benzyl]-6,8-dimethylpurin]-2-yl-3-oxypropyl]pyridine N-oxide. Although only one tautomeric form is shown in general formula (I) above, those skilled in the art are well aware of the existence of other tautomeric forms, and all such tautomeric forms are of course included within the scope of the present invention. The compounds represented by formulas (I) and (II) will sometimes exist as salts, or sometimes as hydrates or solvates, and all such substances are also included within the scope of the invention.

In general formulas (I) and (II), X is a halogen atom or a group represented by —S—$(CH_2)_n$—A, —SO—$(CH_2)_m$—B, —$SO_2$—$(CH_2)_m$—B, —$OSO_2$—$(CH_2)_m$—B, —OCO—$(CH_2)_m$—B or —OPO(OR)—$(CH_2)_m$—B. In these formulas, n represents an integer of 0–4, A represents an optionally substituted aromatic hydrocarbon group or an optionally substituted heterocyclic residue, m represents an integer of 0–4, B represents an optionally substituted alkyl group, an optionally substituted aromatic hydrocarbon group or an optionally substituted heterocyclic residue, and R represents an optionally substituted alkyl group.

The term "halogen atom" as used throughout the present specification refers to a fluorine atom, chlorine atom, bromine atom or iodine atom. As alkyl groups there may be used, for example, $C_1$–$C_7$ and preferably $C_1$–$C_4$ linear or branched alkyl groups, and more specifically there may be mentioned methyl, ethyl, n-propyl, isopropyl, n-butyl, isobutyl, sec-butyl, t-butyl, n-pentyl, 1,2-dimethylpropyl, 1,1-dimethylpropyl, n-hexyl, 1-methylpentyl, 2-methylpentyl, 3-methylpentyl, 4-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, heptyl, 5-methylhexyl, 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl and the like. As preferred groups there may be mentioned methyl, ethyl and propyl.

There are no particular restrictions on the type of aromatic hydrocarbon group, but phenyl and naphthyl may be preferably mentioned, with phenyl being most preferred. There are also no particular restrictions on the type of heterocyclic residue, and for example, a heterocyclic residue having 1 to hetero atoms selected from oxygen atom, sulfur atom and nitrogen atom and having 5 to 10 ring-constituting atoms may be used., such as thienyl group, furyl group, pyrrolyl group, imidazolyl group, pyrazolyl group, triazolyl group, tetrazolyl group, oxazolyl group, isooxazolyl group, thiazolyl group, isothiazolyl group, pyrrolidinyl group, pyridyl group, pyridazinyl group, pyrazinyl group, pyrimidinyl group, triazinyl group, piperidyl group, piperidino group, morpholinyl group, morpholino group, piperaznyl group, benzimidazolyl group, indolyl group, quinolyl group, naphthylidinyl group, quinazolinyl group and the like, preferably thienyl group, furyl group, pyrrolyl group, imidazolyl group, pyrazolyl group, pyridyl group, pyridazinyl group, pyrazinyl group, pyrimidinyl group, triazinyl group, piperidyl group, piperidino group, morpholinyl group, morpholino group, piperazinyl group, benzimidazolyl group and the like, more preferably a 6-membered heterocyclic residue having one or two nitrogen atoms as the hetero atom(s), for example, pyridyl group, pyridazinyl group, pyrazinyl group, pyrimidinyl group, triazinyl group, piperidyl group, piperidino group, morpholinyl group, morpholino group, piperazinyl group and the like.

There are no particular restrictions on the number of substituents, positions of substituents or types of substituents introduced into the aromatic hydrocarbon group, heterocyclic residue and alkyl group, but they are preferably alkyl groups or halogen atoms. It is preferred for m to be 0. X is preferably a halogen atom or —S—$(CH_2)$—A, —$SO_2$—$(CH_2)_m$—B, —$OSO_2$—$(CH_2)_m$—B or —OCO—$(CH_2)$—B, and more preferably a halogen atom or a methanesulfonyl, para-toluenesulfonyl, benzenesulfonyl, para-toluenesulfoxy, methanesulfoxy, phenylthio or trifluoroacetoxy group. Particularly preferred are halogen atoms, with chlorine atoms being most preferred.

The compound of formula (I) may be converted to a compound of formula (II) by reaction with compound (VI) according to the process outlined by the following scheme, and the compound of formula (II) may then be condensed with 3-(4-pyridine)-propanol and the resulting 4-[[9-[(3-cyclopentyloxy-4-methoxy)benzyl]-6,8-dimethylpurin]-2-yl-3-oxypropyl]pyridine oxidized for conversion to its N-oxide and subsequently subjected to treatment under the hydrous conditions described above to produce the dihydrate of the present invention.

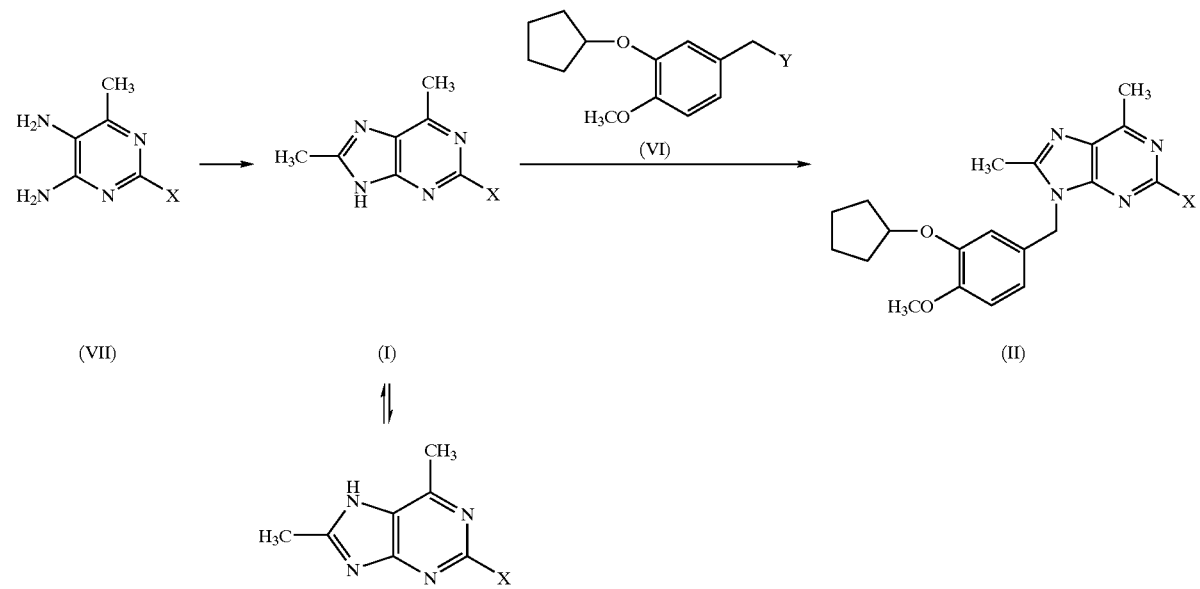

-continued

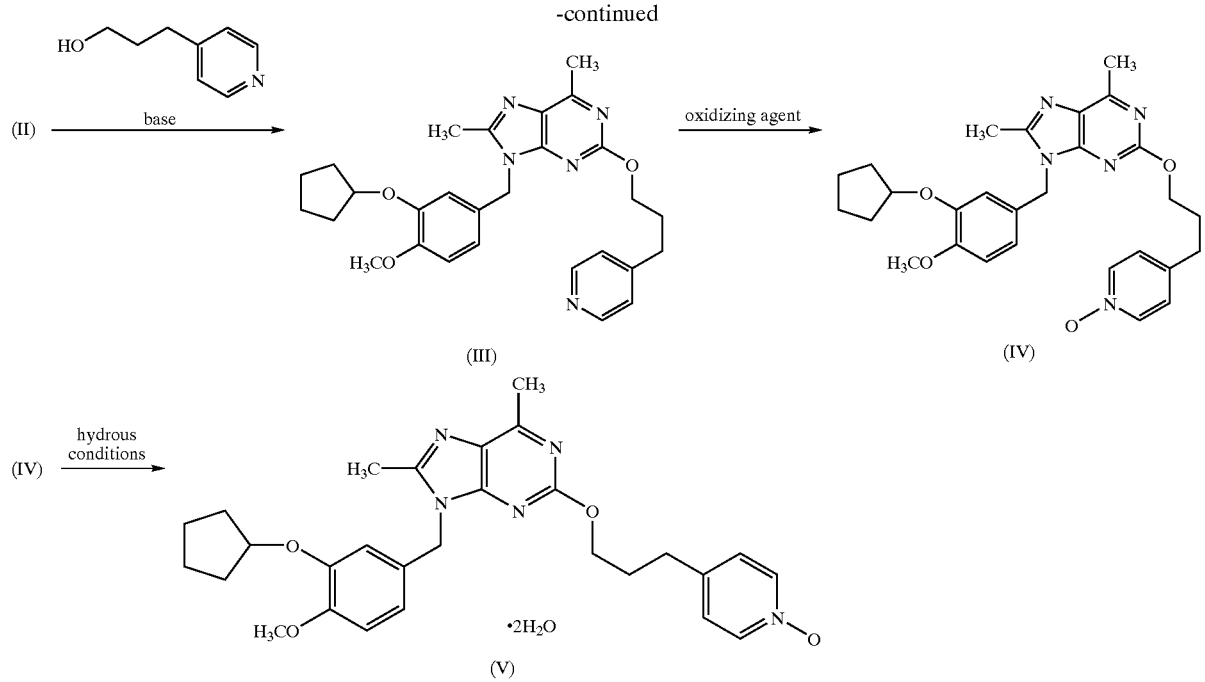

[In the above scheme, X has the definition given above, Y represents a halogen atom or a group represented by —OSO$_2$—(CH$_2$)$_m$—B, —OCO—(CH$_2$)$_m$—B or —OPO(OR)—(CH$_2$)$_m$—B (wherein m represents an integer of 0–4, B represents an optionally substituted alkyl group, an optionally substituted aromatic hydrocarbon group or an optionally substituted heterocyclic residue, and R represents an optionally substituted alkyl group), with two tautomeric forms being indicated for the compound represented by formula (I).]

Compound (I) is obtained by reacting compound (VII) with from one equivalent to a solvent amount of an orthoacetic acid ester in acetic anhydride, acetic acid or a mixture thereof. If necessary, a solvent such as N-methylpyrrolidone, dimethylformamide, dimethylacetamide or dimethylimidazolidinone may be used, and the reaction may be conducted with addition of 0.01–5 equivalents of an acid such as para-toluenesulfonic acid, methanesulfonic acid, trifluoromethanesulfonic acid, hydrochloric acid, sulfuric acid or the like. The reaction is normally carried out in a nitrogen or argon stream at a temperature in the range of –20 to 150° C.

Compound (I) and compound (VI) may be condensed to produce compound (II). The condensation is accomplished by reacting compound (I) with 0.5–5 equivalents of compound (VI) in an appropriate solvent such as dimethylsulfoxide, N,N-dimethylformamide, tetrahydrofuran, methylene chloride or water or a mixed solvent comprising a combination of these solvents. The reaction may be carried out in the presence of 1–5 equivalents of an organic base such as triethylamine, pyridine or N,N-diethylaniline or an inorganic base such as sodium carbonate, potassium carbonate or sodium hydroxide, and if necessary it may be carried out with addition of an additive such as potassium iodide, sodium iodide or tetrabutylammonium iodide. The reaction is normally carried out in a nitrogen or argon stream at a temperature in the range of –20 to 150° C.

The condensation of compound (II) and 3-(4-pyridine)-propanol may be accomplished by adding compound (II) and 3-(4-pyridine)-propanol to an appropriate solvent such as N,N-dimethylformamide or tetrahydrofuran or a mixed solvent comprising a combination of these solvents, and then adding 1–5 equivalents of an organic base such as triethylamine, pyridine or N,N-diethylaniline or an inorganic base such as sodium carbonate or sodium hydroxide. The reaction is normally carried out in a nitrogen or argon stream at a temperature in the range of –20 to 150° C. Next, compound (III) may be treated with an appropriate oxidizing agent such as meta-perbenzoic acid, magnesium monoperoxyphthalate, oxone, hydrogen peroxide or peracetic acid to obtain the corresponding N-oxide (IV). After subjecting the obtained N-oxide (IV) to crystallization from the hydrous solvent, suspension washing in the hydrous solvent or exposure to high humidity conditions, it may be dried at low temperature to produce the dihydrate of the invention.

A compound represented by formula (II) wherein X is a halogen atom may be produced according to the following scheme.

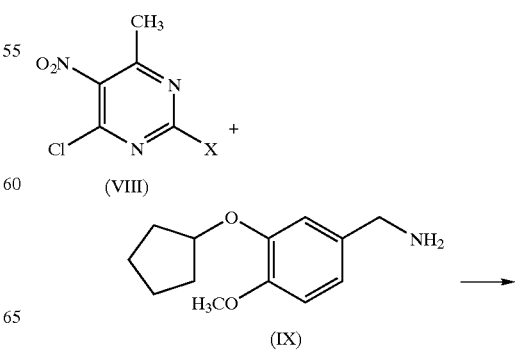

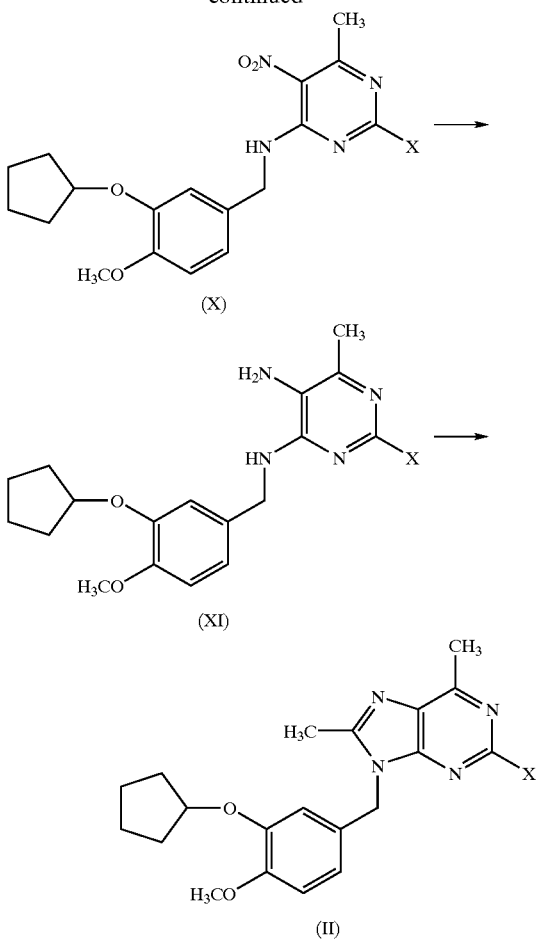

The reaction whereby compound (VIII) and compound (IX) are condensed to obtain compound (X) maybe carried out by adding compound (VIII) and compound (IX) in an appropriate solvent such as N,N-dimethylformamide, tetrahydrofuran, methylene chloride or water or a mixed solvent comprising a combination of these solvents, and then adding and reacting 1–5 equivalents of an organic base such as triethylamine, pyridine or N,N-diethylaniline or an inorganic base such as sodium carbonate or sodium hydroxide. The reaction is normally carried out in a nitrogen or argon stream at a temperature in the range of −20 to 150° C.

The reaction whereby compound (X) is reduced to obtain compound (XI) may be carried out by dissolving compound (X) in a solvent such as methanol, ethanol or tetrahydrofuran or a mixed solvent comprising a combination of these solvents, and then adding 10–100 wt % of a catalyst such as Raney nickel, palladium carbon, palladium carbon hydroxide or platinum and carrying out the reaction from room temperature to 60° C. under a hydrogen stream or pressure. Next, compound (XI) may be reacted with 1–5 equivalents of a reactant such as ortho-triethyl acetate without a solvent or in the presence of 1–5 equivalents of an organic acid such as acetic acid, trifluoroacetic acid or tosylic acid or an inorganic acid such as hydrochloric acid, to obtain compound (II). This reaction is normally carried out in a range from room temperature to 250° C.

The processes for production of compounds according to the present invention represented by formulas (I) and (II) are not restricted to the production processes described above. The production processes for the compounds in the schemes outlined above are explained concretely and in detail in the examples of the present specification. Thus, a person skilled in the art can, by referring to the general explanation given above and the concrete explanation in the examples, produce any of the compounds included by formulas (I) and (II).

The present invention will now be explained in greater detail by way of examples and test examples, with the understanding that the scope of the present invention is in no way limited by these examples and test examples. The compound reference numerals used in the examples correspond to the compound reference numerals in the above schemes.

EXAMPLE 1

Synthesis of 2-chloro-4-(3-cyclopentyloxy-4-methoxybenzylamino)-5-nitro-6-methylpyrimidine (Compound (X))

2,4-Dichloro-5-nitro-6-methylpyrimidine (2.0 g) was dissolved in tetrahydrofuran (14 ml), and added with a solution of 3-cyclopentyloxy-4-methoxybenzylamine (2.25 g) dissolved in tetrahydrofuran (7 ml) with stirring and cooling on a salt-ice bath (−10° C.). Then, the mixture was added dropwise with triethylamine (1.4 ml), and stirred for 30 minutes on a salt-ice bath (−10° C.). The reaction mixture was further added with saturated brine, and then extracted with ethyl acetate. The organic layer was dried over anhydrous sodium sulfate and concentrated under reduced pressure, and the resulting residue was suspended and washed in a mixed solvent of ether and hexane (50:50) to obtain 3.11 g of the title compound.

$^1$H-NMR (CDCl$_3$) δ ppm: 1.59–1.64 (m, 2H), 1.80–1.96 (m, 6H), 2.73 (s, 3H), 3.84 (s, 3H), 4.70 (d, 2H, J=5.4 Hz), 4.74–4.79 (m, 1H), 6.83–6.91 (m, 3H), 8.36 (bs, 1H)

EXAMPLE 2

Synthesis of 5-amino-4-(3-cyclopentyloxy-4-methoxybenzylamino)-2-chloro-6-methylpyridine (Compound (XI))

2-Chloro-4-(3-cyclopentyloxy-4-methoxybenzyl)-5-nitro-6-methylpyrimidine (2.0 g) was dissolved in tetrahydrofuran (14 ml), and the solution was added with methanol (14 ml) and further added with Raney Nickel (1.8 g) under nitrogen atmosphere. The mixture was stirred at room temperature under hydrogen gas atmosphere for 4.5 hours. After the reaction was completed, the reaction suspension was filtered through Celite under nitrogen atmosphere while washing with methanol. The resulting organic layer was concentrated under reduced pressure, and the residue was recrystallized from ether to obtain 1.65 g of the title compound.

$^1$H-NMR (CDCl$_3$) δ ppm: 1.57–1.66 (m, 2H), 1.78–1.97 (m, 6H), 2.31 (s, 3H), 2.90 (bs, 2H), 3.83 (s, 3H), 4.54 (d, 2H, J=5.4 Hz), 4.71–4.77 (m, 1H), 5.30 (bs, 1H), 6.79–6.93 (m, 3H),

EXAMPLE 3

Synthesis of 2-chloro-9-[(3-cyclopentyloxy-4-methoxy)benzyl]-6,8-dimethylpurine (Compound (II))

5-Amino-4-(3-cyclopentyloxy-4-methoxybenzylamino)-2-chloro-6-methylpyrimidine (20.0 g) was added with triethyl orthoacetate (8.9 g) and acetic acid (3.3 g), and the mixture was heated for 3 hours with stirring under heating at 100° C., while ethanol generated during the reaction was removed from the reaction system. After the reaction was completed, the reaction mixture was cooled to room temperature and diluted by adding methylene chloride. The mixture was washed with saturated aqueous sodium hydrogencarbonate, and then with saturated brine. The organic layer was dried over anhydrous magnesium sulfate, and concentrated under reduced pressure. The residue was purified by silica gel column chromatography (chloroform:ethyl acetate=80:20) to obtain 18.9 g of the title compound.

$^1$H-NMR (CDCl$_3$) δ ppm: 1.59–1.63 (m, 2H), 1.76–1.90 (m, 6H), 2.58 (s, 3H), 2.80 (s, 3H), 3.81 (s, 3H), 4.64–4.68 (m, 1H), 5.28 (s, 2H), 6.70 (dd, 1H, J=8.2, 2.0 Hz), 6.78 (d, 1H, J=8.2 Hz), 6.88 (d, H, J=2.0 Hz)

EXAMPLE 4

Synthesis of 2-chloro-9-[(3-cyclopentyloxy-4-methoxy)benzyl]-6,8-dimethylpurine (Compound (II))

After adding 8.3 ml of dimethylsulfoxide, 1.86 g of anhydrous potassium carbonate, 3.0 g of potassium iodide and 1.63 g of 3-cyclopentyloxy-4-methoxybenzyl chloride to 0.83 g of 2-chloro-6,8-dimethylpurine, the mixture was stirred at room temperature for 4.5 hours. After completion of the reaction, the reaction solution was cooled to room temperature and then an ethyl acetate/n-heptane mixed solvent was added thereto for dilation. After washing the mixture solution with water, the organic layer was dried over anhydrous magnesium sulfate and concentrated under reduced pressure. The residue was purified by silica gel column chromatography (chloroform:methanol=98:2) to obtain 1.37 g of the title compound.

$^1$H-NMR (CDCl$_3$) δppm: 1.50–1.94 (m, 8H) 2.59 (s, 3H), 2.81 (s, 3H), 3.82 (s, 3H), 4.64–4.68 (m, 1H), 5.29 (s, 2H), 6.71 (dd, 1H, J=8.2, 2.0 Hz), 6.78 (d, 1H, J=8.2 Hz), 6.88 (d, 1H, J=2.0 Hz)

EXAMPLE 5

Synthesis of 2-chloro-6,8-dimethylpurine (Compound (I))

After adding 10.1 ml of ortho-triethyl acetate, 0.23 g of para-toluenesulfonic acid and 73 ml of 2-methylpyrrolidone to 7.6 g of 4,5-diamino-2-chloro-6-methylpyrimidine, the mixture was heated at 100° C. and then heated and stirred while removing out of the system the ethanol produced during the reaction. After disappearance of the 4,5-diamino-2-chloro-6-methylpyrimidine, the reaction solution was further heated and stirred at 180° C. for 2 hours. After cooling to room temperature, chloroform was added thereto for dilution. The mixture solution was washed with water and then washed with saturated brine, after which the organic layer was dried over anhydrous magnesium sulfate and concentrated under reduced pressure. The residue was purified by silica gel column chromatography (chloroform:methanol=95.5) to obtain 1.55 g of the title compound.

$^1$H-NMR (CDCl$_3$) δppm: 2.74 (s, 3H), 2.84 (s, 3H)

EXAMPLE 6

Synthesis of 9-[(3-cyclopentyloxy-4-methoxy)benzyl]-6,8-dimethyl-2-[3-(4-pyridyl)propyloxy] purine (Compound (III))

4-Pyridinepropanol (29.91 g) was dissolved in tetrahydrofuran (560 ml), and the solution was added with 60% sodium hydride (8.72 g) and stirred at room temperature for 15 minutes. The mixture was added portionwise with 2-chloro-9-[(3-cyclopentyloxy-4-methoxy)benzyl]-6,8-dimethylpurine (59.10 g) and refluxed by heating for 2 hours. The reaction mixture was cooled and concentrated under reduced pressure, and then the mixture was added with water and extracted with ethylacetate. The organic layer was washed with saturated brine, dried over anhydrous magnesium sulfate, and then concentrated under reduced pressure. The residue was purified by silica gel column chromatography (chloroform:methanol=90:10) to obtain 68.19 g of the title compound.

$^1$H-NMR (CDCl$_3$) δ ppm: 1.54–1.81 (m, 8H), 2.15–2.22 (m, 2H), 2.86 (t, 2H, J=6.9 Hz), 3.80 (s, 3H), 4.43 (t, 2H, J=6.9 Hz) 4.62–4.64 (m, 1H), 5.23 (s, 2H), 6.67–6.79 (m, 3H), 7.16 (d, 2H, J=6.7 Hz), 8.48 (d, 2H, J=6.7 Hz)

EXAMPLE 7

Synthesis of Anhydrous of 4-[[9-[(3-cyclopentyloxy-4-methoxy)benzyl]-6,8-dimethylpurine]-2-yl-3-oxypropyl] Pyridine N-oxide (Compound (IV))

After dissolving 3 g of 9-[(3-cyclopentyloxy-4-methoxy)benzyl]-6,8-dimethyl-2-[3-[4-pyridyl)propoxy] purine in 30 ml of methylene chloride, a solution of 3.85 g of MMPP (magnesium monoperoxyphthalate hexahydrate) in 30 ml of distilled water was added thereto while cooling on ice and the mixture was stirred at room temperature for 3 hours. Upon confirming disappearance of the starting material by TLC, the reaction mixture was poured into an aqueous solution of 5% sodium sulfate while cooling on ice and stirred at room temperature for one hour to decompose the excess MMPP. After extracting the reaction solution with methylene chloride, it was washed with saturated sodium bicarbonate water and then further washed with saturated brine. The obtained organic layer was dried over anhydrous sodium sulfate and concentrated under reduced pressure. The obtained residue was purified by silica gel column chromatography (chloroform:methanol=90:10) and the resulting compound was recrystallized from THF-heptane to obtain 2.22 g of the title compound.

$^1$H-NMR (CDCl$_3$) δppm: 1.56–1.81 (m, 8 H), 2.10–2.19 (m, 2H), 2.51 (s, 3H), 2.75 (s, 3H), 2.85–2.90 (m, 2H), 3.81 (s, 3H), 4.40–4.44 (m, 2H), 4.63–4.64 (m, 1H), 5.24 (s, 2H), 6.65–6.79 (m, 3H), 7.14 (d, 2H, J=6.7 Hz), 8.13 (d, 2H, J=6.7 Hz)

(Measurement of Melting Point)

A small sample was measured out and sandwiched between two preparations and then placed on the hot plate of a melting point measuring apparatus (YANACO-MP, product of Yanagimoto Seisakusho) for heating, and the melting was observed visually. The temperature elevating rate was kept constant at 1–2°/min. (The melting points throughout the present specification were measured by this method unless otherwise specified.)

m.p. 134.5–135.5° C.

EXAMPLE 8

Synthesis of Dihydrate of 4-[[9-[(3-cyclopentyloxy-4-methoxy)benzyl]-6,8-dimethylpurine]-2-yl-3-oxypropyl]pyridine N-oxide (Method A)

Isopropyl alcohol (7 ml) and water (35 ml) were added to 5 g of an anhydrous of 4-[[9-[(3-cyclopentyloxy-4-methoxy)benzyl]-6,8-dimethylpurine]-2-yl-3-oxypropyl)pyridine N-oxide and the mixture was heated to 70° C. while stirring to obtain a uniform mixture, after which it was cooled to room temperature white continuing the stirring to accomplish crystallization. After approximately 3 hours, the precipitated crystals were filtered and dried at 50° C. for 5 hours under reduced pressure (90 mmHg) to obtain 5.06 g of crystals of dihydrate of 4-[[9-[(3-cyclopentyloxy-4-methoxy)benzyl]-6,8-dimethylpurine]-2-yl-3-oxypropyl]pyridine N-oxide. The yield was 95%.

$^1$H-NMR (CDCl$_3$) δppm: 1.55–1.82 (m, 12H), 2.12–2.17 (m, 2H), 2.51 (s, 3H), 2.75 (s, 3H), 2.88 (m, 2H), 3.81 (s, 3H), 4.42 (t, 2H, J=6.2 Hz), 4.64 (m, 1H), 5.24 (s, 2H), 6.65–6.79 (m, 3H), 7.15 (d, 2H, J=6.6 Hz), 8.13 (d, 2H, J=7.2 Hz) m.p. 65–70° C.

Measurement of the melting point according to the method described in the Japanese Pharmacopoeia (13th Revision) gave a value of 101–102° C. The measuring device used was a BUCHI Model 535 melting point measuring apparatus.

Elemental analysis (C$_{28}$H$_{37}$N$_5$O$_6$) Calcd. C: 62.32, H: 6.91, N: 12.98 Found C: 62.42, H: 6.97, N: 12.89

EXAMPLE 9

Synthesis of Dihydrate of 4-[[9-[(3-cyclopentyloxy-4-methoxy)benzyl]-6,8-dimethylpurine]-2-yl-3-oxypropyl]pyridine N-oxide (Method B)

A dihydrate was obtained by allowing 1.5 g of an anhydrous of 4-[[9-[(3-cyclopentyloxy-4-methoxy)benzyl]-6,8-dimethylpurine]-2-yl-3-oxypropyl]pyridine N-oxide to stand for 4 weeks at room temperature with 75% relative humidity. Measurement of the moisture content by the Karl Fischer method confirmed that the dehydrate theoretical content of 6.7% had been maintained.

EXAMPLE 10

Synthesis of Dihydrate of 4-[[9-[(3-cyclopentyloxy-4-methoxy)benzyl]-6,8-dimethylpurine]-2-yl-3-oxypropyl]pyridine N-oxide (Method C)

After measuring out 1 g of an anhydrous of 4-[[9-[(3-cyclopentyloxy-4-methoxy)benzyl]-6,8-dimethylpurine]-2-yl-3-oxypropyl]pyridine N-oxide, water (10 ml) was added and the mixture was heated at 70° C. for 12 hours. After cooling to room temperature, it was filtered and allowed to dry naturally for one week to obtain dihydrate crystals. Measurement of the moisture content by the Karl Fischer method confirmed that the dihydrate theoretical content of 6.9% had been maintained.

Test Example (1) The stability of the dihydrate of the present invention was examined.

After exposing 100 mg of a dihydrate of 4-[[9-[(3-cyclopentyloxy-4-methoxy)benzyl]-6,8-dimethylpurine]-2-yl-3-oxypropyl]pyridine N-oxide (moisture content of 6.7% by the Karl Fischer method) in a dry silica gel-containing desiccator for 3 weeks, the moisture content was measured by the Karl Fischer method, whereby it was confirmed that the dihydrate theoretical content of 6.8% had been maintained.

(2) The PDE IV inhibiting effect of the dihydrate of the invention was examined.

The rolipram used for reference was the compound described in Japanese Unexamined Patent Publication (Kokai) No. 50-157360/1975, the structure of which was indicated under Background Art of the present specification. The specific inhibitory effect of this compound against PDE IV is described in Adv. Second Messenger Phosphoprotein Res., 22, 1(1988) and elsewhere. The crude enzyme was purified from a cytoplasmic fraction of human monocyte-like cell strain U937 by using a Q-Sepharose column according to the method of Nicholson et al. (Br. J. Pharmacol., 97, 889 (1989)]. The enzymatic activity was determined by performing a reaction using 0.4 μM $^3$H-cAMP as the substrate in 50 mM Tris buffer (pH 8.0) containing 0.1 mg/ml BSA, 1 ml of EDTA and 5 mM MgCl$_2$ at 30° C. for 15 minutes, and then separating the produced $^3$H-5'-AMP using a cation exchange column and measuring its radioactivity according to the method of Hidaka et al. [Biochem. Med., 10, 301 (1974)]. After a test compound was added, the reaction mixture was incubated at 30° C. for 15 minutes, and then added with the substrate. Inhibitory ratio at each concentration was obtained based on the reaction performed with no addition of a test compound which was taken as 100%, and a concentration for 50% inhibition (IC$_{50}$) was calculated by the plot analysis. The results showed an IC$_{50}$(M) of $3.41 \times 10^{-9}$ for the dihydrate of the present invention and an IC$_{50}$(M) of $5.02 \times 10^{-7}$ for rolipram.

INDUSTRIAL APPLICABILITY

The dihydrate of the present invention is stable and exhibits an excellent inhibitory effect against PDE IV, and is therefore useful as an active ingredient for drugs used for remedy and/or prevention of asthma, COPD and/or other inflammatory diseases. The compounds represented by general formulas (I) and (II) are useful as intermediates in the production of the hydrate of the present invention.

What is claimed is:

1. A compound represented by the following formula (I), or a salt thereof:

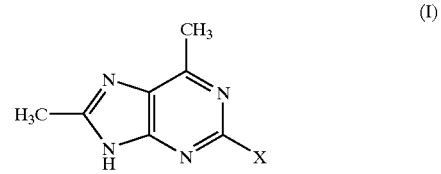

where X is a halogen atom or a group represented by —S—(CH$_2$)$_n$—A, —SO—(CH$_2$)$_m$—B, —SO$_2$—(CH$_2$)$_m$—B, —OSO$_2$—(CH$_2$)$_m$—B, —OCO—(CH$_2$)$_m$—B or —OPO(OR)—(CH$_2$)$_m$—B, wherein n represents an integer of 0–4, A represents an optionally substituted aromatic hydrocarbon group or an optionally substituted heterocyclic residue having 1 to 4 hetero atoms selected from an oxygen atom, sulfur atom and nitrogen atom and having 5 to 10 ring-constituent atoms, m represents an integer of 0–4, B represents an optionally substituted alkyl group, an optionally substituted aromatic hydrocarbon group or an optionally substituted heterocyclic residue having 1 to 4 hetero atoms selected from an oxygen atom, sulfur atom and nitrogen atom and having 5 to 10 ring-constituent atoms, and R represents an optionally substituted alkyl group.

2. A compound represented by the following formula (II), or a salt thereof:

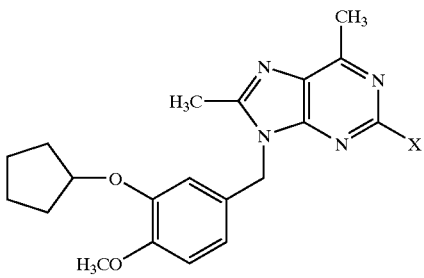

(II)

where X is a group represented by —SO—$(CH_2)_m$—B, —$SO_2$—$(CH_2)_m$—B, —$OSO_2$—$(CH_2)_m$—B, —OCO—$(CH_2)_m$—B or —OPO(OR)—$(CH_2)_m$—B, wherein n represents an integer of 0–4, A represents an optionally substituted aromatic hydrocarbon group or an optionally substituted heterocyclic residue having 1 to 4 hetero atoms selected from an oxygen atom, sulfur atom and nitrogen atom and having 5 to 10 ring-constituent atoms, m represents an integer of 0–4, B represents an optionally substituted alkyl group, an optionally substituted aromatic hydrocarbon group or an optionally substituted heterocyclic residue having 1 to 4 hetero atoms selected from an oxygen atom, sulfur atom and nitrogen atom and having 5 to 10 ring-constituent atoms, and R represents an optionally substituted alkyl group.

3. A method for producing a compound represented by the following formula (II) or a salt thereof, comprising reacting a compound represented by the following formula (I) or a salt thereof and a compound represented by the following formula (VI) or a salt thereof:

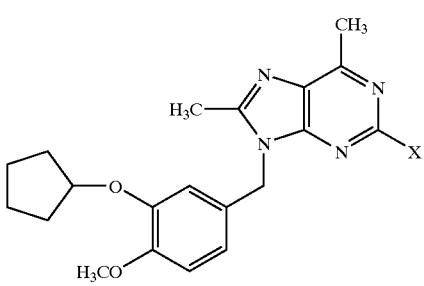

(II)

where X is a halogen atom or a group represented by —S—$(CH_2)_n$—A, —SO—$(CH_2)_m$—B, —$SO_2$—$(CH_2)_m$—B, —$OSO_2$—$(CH_2)_m$—B, —OCO—$(CH_2)_m$—B or —OPO(OR)—$(CH_2)_m$—B, wherein n represents an integer of 0–4, A represents an optionally substituted aromatic hydrocarbon group or an optionally substituted heterocyclic residue having 1 to 4 hetero atoms selected from an oxygen atom, sulfur atom and nitrogen atom and having 5 to 10 ring-constituent atoms, m represents an integer of 0–4, B represents an optionally substituted alkyl group, an optionally substituted aromatic hydrocarbon group or an optionally substituted heterocyclic residue, and R represents an optionally substituted alkyl group;

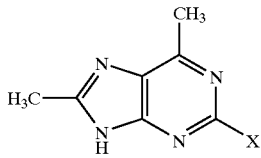

(I)

where X is a halogen atom or a group represented by —S—$(CH_2)_n$—A, —SO—$(CH_2)_m$—B, —$SO_2$—$(CH_2)_m$—B, —$OSO_2$—$(CH_2)_m$—B, —OCO—$(CH_2)_m$—B or —OPO(OR)—$(CH_2)_m$—B, wherein n represents an integer of 0–4, A represents an optionally substituted aromatic hydrocarbon group or an optionally substituted heterocyclic residue having 1 to 4 hetero atoms selected from an oxygen atom, sulfur atom and nitrogen atom and having 5 to 10 ring-constituent atoms, m represents an integer of 0–4, B represents an optionally substituted alkyl group, an optionally substituted aromatic hydrocarbon group or an optionally substituted heterocyclic residue having 1 to 4 hetero atoms selected from an oxygen atom, sulfur atom and nitrogen atom and having 5 to 10 ring-constituent atoms, and R represents an optionally substituted alkyl group;

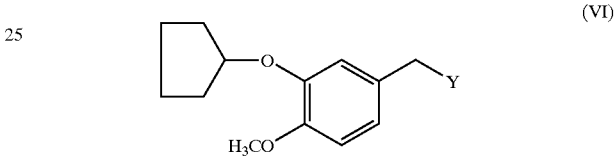

(VI)

where Y is a halogen atom or a group represented by —$OSO_2$—$(CH_2)_m$—B, —OCO—$(CH_2)_m$—B or —OPO(OR)—$(CH_2)_m$—B, wherein m represents an integer of 0–4, B represents an optionally substituted alkyl group, an optionally substituted aromatic hydrocarbon group or an optionally substituted heterocyclic residue having 1 to 4 hetero atoms selected from an oxygen atom, sulfur atom and nitrogen atom and having 5 to 10 ring-constituent atoms, and R represents an optionally substituted alkyl group.

4. A method for producing 4-[[9-[(3-cyclopentyloxy-4-methoxy)benzyl]-6,8-dimethylpurin]-2-yl-oxypropyl] pyridine N oxide, comprising:

reacting a compound produced by the method of the claim 3 or a salt thereof and a compound represented by the following formula,

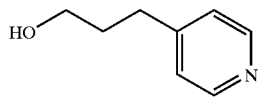

and reacting the resulting compound with an oxidizing agent.

5. A method for producing a dihydrate of 4-[[9-[(3-cyclopentyloxy-4-methoxy)benzyl]-6,8-dimethylpurin]-2-yl-oxypropyl] pyridine N oxide, comprising:
reacting a compound produced by the method of the claim 3 or a salt thereof and a compound represented by the following formula,

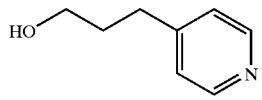

reacting the resulting compound with an oxidizing agent, and adding water.

* * * * *

UNITED STATES PATENT AND TRADEMARK OFFICE
CERTIFICATE OF CORRECTION

PATENT NO.   : 6,919,455 B2  
DATED        : July 19, 2005  
INVENTOR(S)  : K. Sekiya et al.

It is certified that error appears in the above-identified patent and that said Letters Patent is hereby corrected as shown below:

<u>Title page</u>,  
Item [56], References Cited, OTHER PUBLICATIONS, insert the following references:  
-- First Page of JP8-501318  
  Giembycz, Drugs 59(2), 193 (2000). --.

Signed and Sealed this

Fourteenth Day of February, 2006

JON W. DUDAS  
*Director of the United States Patent and Trademark Office*